United States Patent
Setomaru et al.

(10) Patent No.: US 10,073,111 B2
(45) Date of Patent: Sep. 11, 2018

(54) AUTOMATIC ANALYSIS DEVICE

(71) Applicant: Hitachi High-Technologies Corporation, Minato-ku, Tokyo (JP)

(72) Inventors: Takeshi Setomaru, Tokyo (JP); Hideyasu Chiba, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 61 days.

(21) Appl. No.: 15/319,416

(22) PCT Filed: Jun. 10, 2015

(86) PCT No.: PCT/JP2015/066765
§ 371 (c)(1),
(2) Date: Dec. 16, 2016

(87) PCT Pub. No.: WO2016/017294
PCT Pub. Date: Feb. 4, 2016

(65) Prior Publication Data
US 2017/0153259 A1    Jun. 1, 2017

(30) Foreign Application Priority Data

Jul. 30, 2014   (JP) ................................ 2014-154868

(51) Int. Cl.
*G01N 35/02*   (2006.01)
*G01N 35/10*   (2006.01)
(Continued)

(52) U.S. Cl.
CPC ............ *G01N 35/025* (2013.01); *G01N 21/77* (2013.01); *G01N 35/1009* (2013.01); *G01N 35/00584* (2013.01)

(58) Field of Classification Search
None
See application file for complete search history.

(56) References Cited

U.S. PATENT DOCUMENTS

2002/0025275 A1   2/2002   Oonuma et al.
2004/0208787 A1   10/2004  Takahashi et al.
2015/0346230 A1   12/2015  Setomaru et al.

FOREIGN PATENT DOCUMENTS

EP   2 952 903 A1   12/2015
JP   2000-131328 A   5/2000
(Continued)

OTHER PUBLICATIONS

International Preliminary Report on Patentability (PCT/IB/338) issued in PCT Application No. PCT/JP2015/066765 dated Feb. 2, 2017, including English translation of document C3 (International Preliminary Report on Patentability (PCT/IPEA/409)) previously filed on Dec. 16, 2016 (five (5) pages).

(Continued)

*Primary Examiner* — Patricia Kathryn Wright
(74) *Attorney, Agent, or Firm* — Crowell & Moring LLP (57) ABSTRACT

The present invention achieves an automatic analysis device which has a probe guard for which the range of motion for accessing a specimen container installation section is small and which can be moved without being removed from a specimen installation section. The directions of movement of a probe guard are the vertical direction of a specimen container erection mechanism and the horizontal direction within an upper region of the specimen container erection mechanism, and a specimen container can be accessed without the need to move the probe guard to outside the upper region of the specimen container erection mechanism. Accordingly, it is possible to achieve an automatic analysis device which has a probe guard for which the range of motion for accessing a specimen installation section is small and which can be moved without being removed from a specimen container erection mechanism.

10 Claims, 11 Drawing Sheets

(51) Int. Cl.
*G01N 21/77* (2006.01)
*G01N 35/00* (2006.01)

(56) References Cited

FOREIGN PATENT DOCUMENTS

| | | |
|---|---|---|
| JP | 2002-71696 A | 3/2002 |
| JP | 2004-317269 A | 11/2004 |
| JP | 2006-284609 A | 10/2006 |
| JP | 2010-91427 A | 4/2010 |
| JP | 2014-211401 A | 11/2014 |
| WO | WO 2014/119486 A1 | 8/2014 |

OTHER PUBLICATIONS

International Search Report (PCT/ISA/210) issued in PCT Application No. PCT/JP2015/066765 dated Sep. 8, 2015 with English translation (5 pages).
Japanese-language Written Opinion (PCT/ISA/237) issued in PCT Application No. PCT/JP2015/066765 dated Sep. 8, 2015 (6 pages).
International Preliminary Report on Patentability (PCT/IPEA/409) issued in PCT Application No. PCT/JP2015/066765 dated Jun. 14, 2016 (4 pages).
European Search Report issued in counterpart European Application No. 15826394.7 dated Apr. 26, 2018 (nine (9) pages).

WHEN PROBE GUARD IS PLACED

[FIG. 15]

WHEN PROBE GUARD IS REMOVED
(WHEN SHUTTER OPERATES)

[FIG. 16]

AUTOMATIC ANALYSIS DEVICE

TECHNICAL FIELD

The present invention relates to an automatic analysis device for analyzing a component in a biological sample such as blood or urine.

BACKGROUND ART

In an automatic analysis device for clinical examination, a probe for, for example, sucking/discharging a specimen and a reagent is provided. The probe thereof has a tapered sharp tip for, for example, dispensing an extremely small amount of a specimen/reagent.

In the automatic analysis device, it is necessary to have a structure or take measures to reduce a risk of contact between a finger of an operator and a tip portion of the probe in order to secure safety of the operator. An example thereof is a probe guard, and this probe guard is a component installed on the periphery of a track of the probe in order to limit the operator's access to the tip portion of the probe or urge caution in the operator's access to the tip portion of the probe.

An example of the probe guard is a specimen contact prevention plate disclosed in PTL 1.

CITATION LIST

Patent Literature(s)

PTL 1: JP-A-2006-284609

SUMMARY OF INVENTION

Technical Problem(s)

The above-mentioned probe guard is provided for limiting access to the tip portion of the probe and urging caution on the tip portion of the probe in order to secure safety of an operator and is installed on the periphery of the track of the tip portion of the probe. As a result, the probe guard has a function of limiting an operator's access to a specimen installation section, which may lose convenience of operation at the same time.

Herein, the specimen contact prevention plate disclosed in PTL 1 retracts from a position above a sample disk when an operator presses the specimen contact prevention plate with his/her hand. In other words, the specimen contact prevention plate disclosed in PTL 1 has a fulcrum in a lower part thereof and retracts from the position above the sample disk by rotating around this fulcrum.

In the case where a specimen contact prevention plate can retract from a position above a sample disk as disclosed in PTL 1, an operator can access a region guarded by the specimen contact prevention plate.

However, in the case of the specimen contact prevention plate disclosed in PTL 1, an operating range for retracting from a position above the sample disk is large, and therefore it is necessary to secure a space therefor.

A large automatic analysis device can secure an operating range (operating space) for retracting the specimen contact prevention plate from a position above the sample disk. However, it is difficult for a small automatic analysis device to secure an operating space for retraction.

Thus, in the case where the specimen contact prevention plate is applied to a small automatic analysis device, it is necessary to completely remove the specimen contact prevention plate from the automatic analysis device in order that an operator accesses a region guarded by the specimen contact prevention plate. Therefore, operation by the operator becomes complicated, which leads to decrease in efficiency of analysis of specimens.

An object of the invention is to realize an automatic analysis device having a small moving range for accessing a specimen container installation section and including a probe guard capable of moving without being removed from the specimen container installation section.

Solution to Problem(s)

In order to achieve the object, the invention is configured as follows.

An automatic analysis device includes: a specimen container arrangement mechanism; a reagent container arrangement mechanism; a reaction container arrangement mechanism; a specimen sampling mechanism including a probe for sucking a specimen from a specimen container arranged in the specimen container arrangement mechanism and discharging the specimen to a reaction container arranged in the reaction container arrangement mechanism; a reagent sampling mechanism configured to suck a reagent from a reagent container arranged in the reagent container arrangement mechanism and discharge the reagent to the reaction container; a photometer configured to analyze the specimen in the reaction container; a control unit configured to control operation of the specimen container arrangement mechanism, the reagent container arrangement mechanism, the reaction container arrangement mechanism, the specimen sampling mechanism, and the reagent sampling mechanism; a probe guard having a guard wall for surrounding the probe when the probe of the specimen sampling mechanism positions above the specimen container arrangement mechanism; and a vertical and horizontal movement restriction section configured to restrict movement of the probe guard in vertical and horizontal directions in a state in which the probe guard positions above the specimen container arrangement mechanism.

Advantageous Effects of Invention

It is possible to realize an automatic analysis device having a small moving range for accessing a specimen container installation section and including a probe guard capable of moving without being removed from the specimen container installation section.

DESCRIPTION OF EMBODIMENTS

Hereinafter, an embodiment of the invention will be described with reference to the attached drawings.

Note that members having the same function are basically denoted by the same reference symbol in all the drawings for showing the embodiment of the invention, and repeated description thereof is omitted as much as possible.

EXAMPLE

Figure 1:
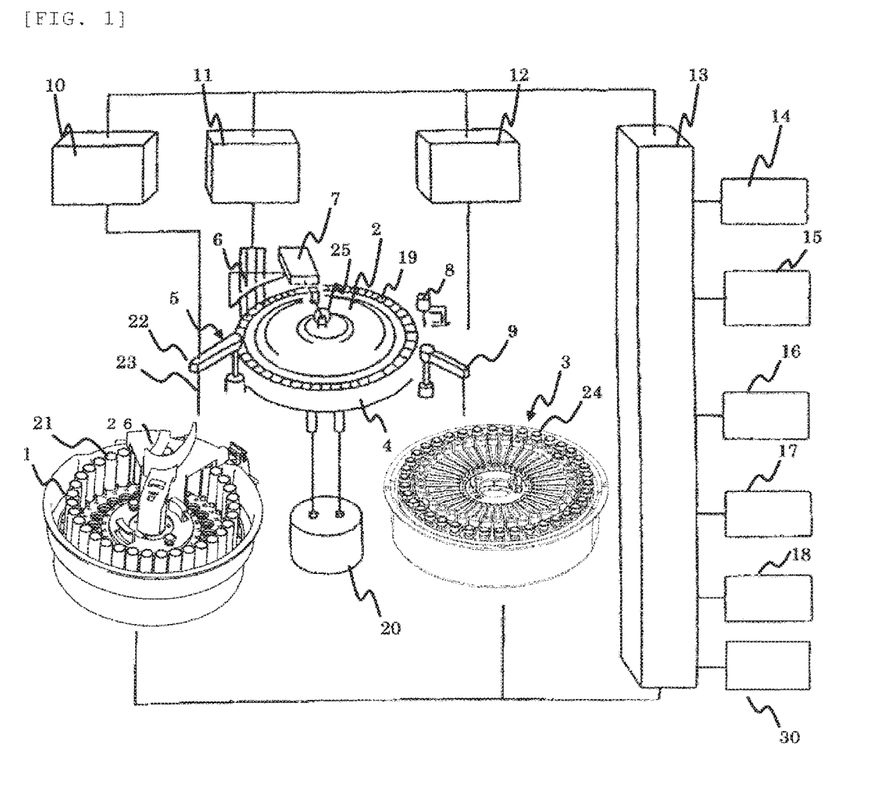
FIG. 1 is the whole configuration diagram of an automatic analysis device to which an example of the invention is applied.

FIG. 1 is the whole configuration diagram of an automatic analysis device to which an example of the invention is applied.

In FIG. 1, the automatic analysis device includes a specimen container erection mechanism (specimen container arrangement mechanism) 1, a reaction vessel mechanism (reaction container arrangement mechanism) 2, a reagent cooling mechanism (reagent container arrangement mechanism) 3, a photometer 7, a light source 25, and an LCD (display section) 16 with a touchscreen.

The reaction vessel mechanism 2 is provided to be intermittently rotated, and a large number of reaction cells 19 made of a light transmitting material are mounted on a disk in a circumferential direction. The reaction cells 19 are maintained at a predetermined temperature (for example, 37° C.) by a thermostatic vessel 4. A temperature of a fluid in the thermostatic vessel 4 is adjusted by a constant temperature maintaining device 20.

A large number of specimen containers 21 containing a biological sample such as blood or urine are placed on the specimen container erection mechanism 1 in the circumferential direction, the specimen containers 21 being placed in two rows in the example shown in FIG. 1. Further, a specimen sampling mechanism 5 is arranged on the periphery of the specimen container erection mechanism 1. This specimen sampling mechanism 5 mainly includes a movable arm 22 and a sampling nozzle 23 attached thereto. With this configuration, in order to dispense a sample, the specimen sampling mechanism 5 appropriately moves the sampling nozzle (probe) 23 to a dispensing position by using the movable arm 22 and causes the sampling nozzle to suck a predetermined amount of the sample from the specimen container 21 positioned at a suction position of the specimen container erection mechanism 1 and discharge the sample into the reaction cell 19 positioned at a discharging position on the reaction vessel mechanism 2.

In the reagent cooling mechanism 3, a plurality of reagent bottles 24 are placed in a circumferential direction of the reagent cooling mechanism 3. Those reagent bottles 24 contain a reagent solution corresponding to an analysis item that can be analyzed by the automatic analysis device.

Further, a reagent pipetting mechanism (reagent sampling mechanism) 9 that is a mechanism substantially similar to the specimen sampling mechanism 5 is arranged in the vicinity of the reagent cooling mechanism 3. In order to dispense a reagent, a pipette nozzle included in this sucks the reagent from the reagent bottle 24 corresponding to an inspection item positioned at a reagent receiving position on the reaction vessel mechanism 2 and discharges the reagent into the corresponding reaction cell 19.

A stirring mechanism 8 is arranged at a position surrounded by the reaction vessel mechanism 2, the reagent cooling mechanism 3, and the reagent pipetting mechanism 9. A mixed liquid of the sample and the reagent contained in the reaction cell 19 is stirred by this stirring mechanism 8 to promote reaction.

Herein, the light source 25 is arranged in the vicinity of the center of the reaction vessel mechanism 2, and the photometer 7 is arranged on the side of an outer circumference of the reaction vessel mechanism 2. A line of the reaction cells 19 that have been stirred is rotationally moved to pass through a photometric position interposed between the light source 25 and the photometer 7. Note that the light source 25 and the photometer 7 constitute a light detection system. The photometer 7 is a multiwavelength photometer for detecting transmitted light or scattered light.

A reaction liquid of the sample and the reagent in each reaction cell 19 is subjected to photometry every time when the reaction cell passes across the photometer 7 during rotation operation of the reaction vessel mechanism 2. An analog signal of scattered light measured for each sample is input to a Log converter/A/D converter 15 via an interface 13. The used reaction cell 19 can be repeatedly used by washing the inside thereof with the use of a reaction cell washing mechanism 6 arranged in the vicinity of the reaction vessel mechanism 2.

Next, a control system and a signal processing system in the automatic analysis device in FIG. 1 will be simply described. A microcomputer (control unit) 14 is connected to a sample dispensing control unit 10, a reagent dispensing control unit 12, and a washing water pump 11 via the interface 13. The microcomputer 14 transmits a command to the sample dispensing control unit 10 to control dispensing operation of the sample. Further, the microcomputer 14 transmits a command to the reagent dispensing control unit 12 to control dispensing operation of the reagent.

Further, the microcomputer 14 is connected to a printer 17 for printing and a storage medium 18. The storage medium 18 is made up of, for example, a hard disk memory or an external memory. Information such as a display level of each screen, an analysis parameter, an analysis item request content, a calibration result, and an analysis result is stored on the storage medium 18.

Next, analysis operation of a sample in the automatic analysis device in FIG. 1 will be described. An analysis parameter regarding an item that can be analyzed by the automatic analysis device is input in advance via an information inputting device such as the LCD 16 with a touchscreen and is stored on the storage medium 18. An operator selects an inspection item requested for each sample by using an operation function screen.

At this time, information such as a patient ID is also input via the LCD 16 with a touchscreen. In order to analyze an inspection item designated for each sample, the sampling nozzle 23 of the specimen sampling mechanism 5 dispenses a predetermined amount of the sample to the reaction cell 19 from the specimen container 21 in accordance with an analysis parameter.

The reaction cell 19 to which the sample has been dispensed is transferred by rotation of the reaction vessel mechanism 2 and is stopped at a reagent receiving position. The pipette nozzle of the reagent pipetting mechanism 9 dispenses a predetermined amount of a reagent solution to the reaction cell 19 in accordance with the analysis parameter of the corresponding inspection item. The order of dispensing the sample and the reagent may be opposite to the order in this example, i.e., the reagent may be dispensed before the sample.

Thereafter, the sample and the reagent are stirred and mixed by the stirring mechanism 8. When the reaction cell 19 passes across the photometric position, transmitted light or scattered light of the reaction liquid is measured by the photometer 7. The measured transmitted light or scattered light is converted by the Log converter/A/D converter 15 into a numerical value in proportion to an amount of light and is stored on the storage medium 18 via the LCD 16 with a touchscreen.

Concentration data is calculated by using this converted numerical value on the basis of a calibration curve measured in advance by an analysis method designated for each inspection item. Component concentration data serving as an analysis result of each inspection item is output to the printer 17.

Before the above measurement operation is executed, the operator performs setting of various parameters needed for analysis measurement and registration of a sample via the LCD 16 with a touchscreen. Further, the operator checks an analysis result after measurement by using the LCD 16 with a touchscreen or printing from the printer 17.

In FIG. 1, a probe guard 26 is attached to the specimen container erection mechanism 1. Further, a probe guard installation presence/absence detection sensor 30 is connected to the microcomputer 14 via the interface 13.

Figure 2:
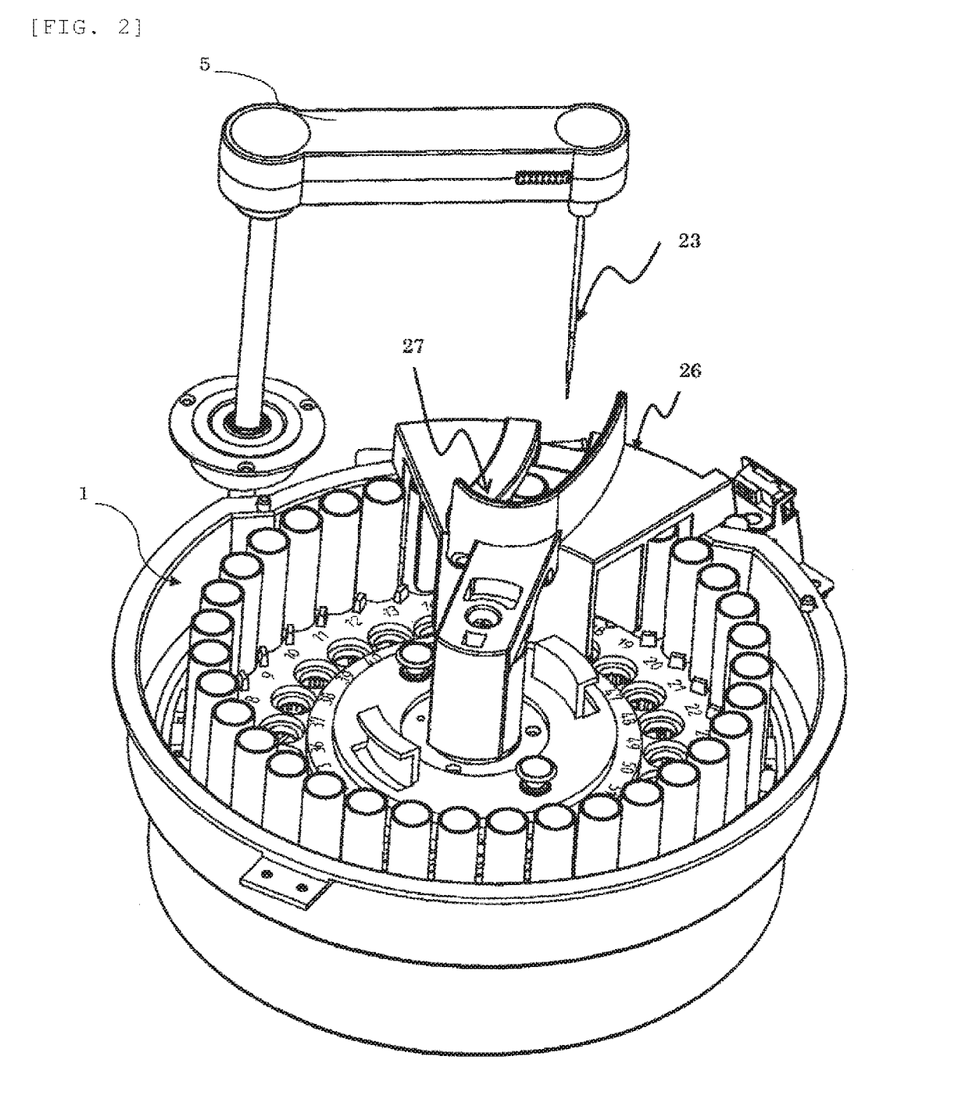
FIG. 2 is an enlarged perspective view of a specimen container erection mechanism and a probe guard in an example of the invention.

FIG. 2 is an enlarged perspective view of the specimen container erection mechanism 1 and the probe guard 26 in an example of the invention.

In FIG. 2, the probe guard 26 is supported by and is fixed to a center portion and an outer circumferential portion of the specimen container erection mechanism 1 to be positioned above the specimen container erection mechanism 1. In the probe guard 26, a guard wall 27 is provided along a moving track of the sampling nozzle 23 of the specimen sampling mechanism 5, and this guard wall 27 blocks an operator's access to the sampling nozzle 23 of the sampling mechanism 5.

Figure 3:
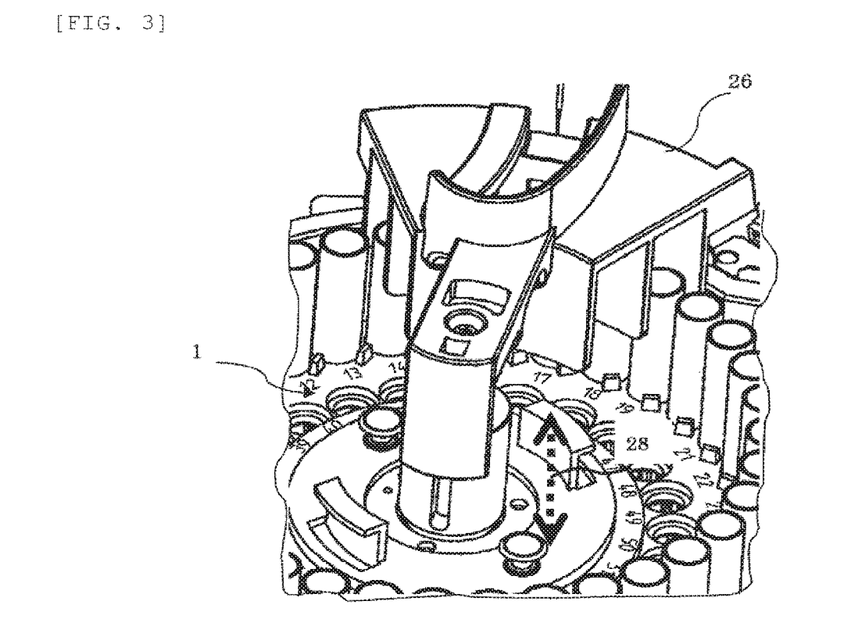
FIG. 3 is a perspective view of a probe guard in an example of the invention.
Figure 4:
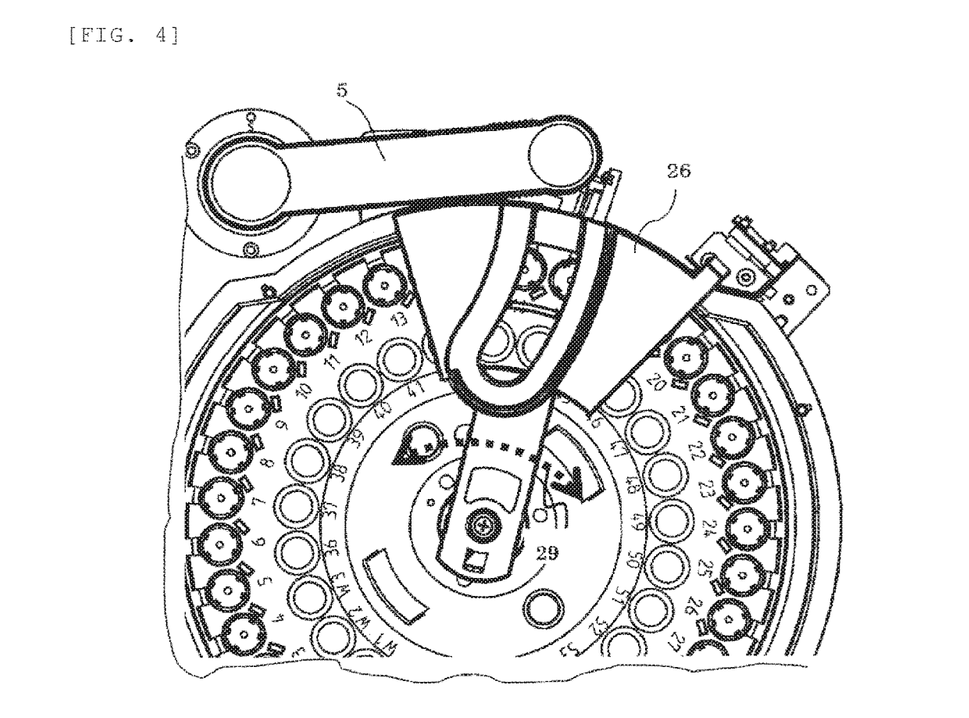
FIG. 4 is a top view of a probe guard in an example of the invention.

FIG. 3 is a perspective view of the probe guard 26, and FIG. 4 is a top view of the probe guard 26. FIG. 3 and FIG. 4 show a state in which the probe guard 26 is moved without being removed from a position at which the probe guard 26 is fixed to the specimen container erection mechanism 1.

In FIG. 3 and FIG. 4, the probe guard 26 can be moved in a vertical direction 28 and a horizontal direction 29 in a state in which the probe guard 26 is attached to the specimen container erection mechanism 1, and an area in which access is limited due to installation of the probe guard 26 can be accessed by moving the probe guard 26. For example, the probe guard 26 can be moved in the vertical direction within the range of 5 to 10 cm and can be moved in the horizontal direction (rotation direction) within the range corresponding to two right sample containers and two left sample containers in which access is limited by the probe guard 26.

Figure 5:
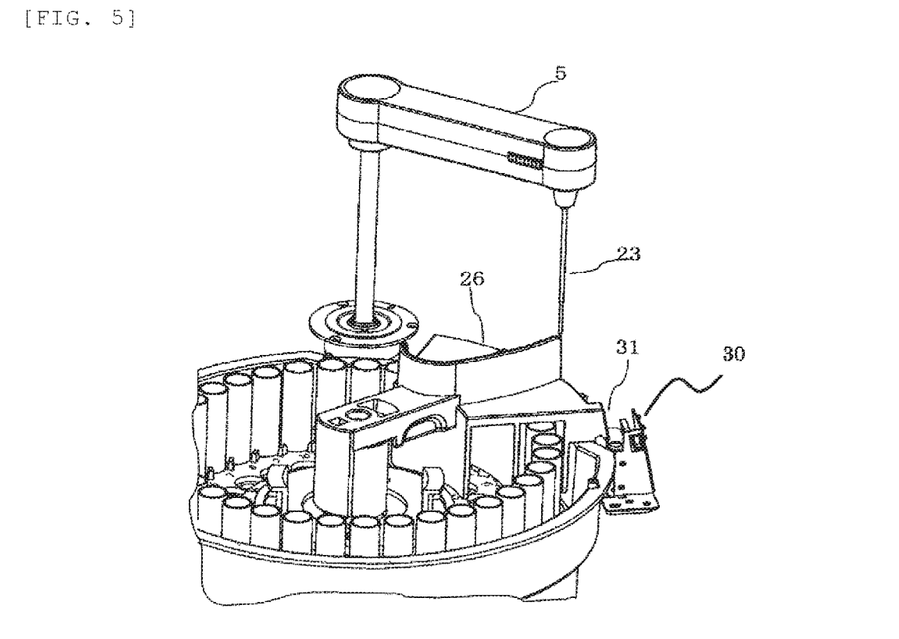
FIG. 5 shows a positional relationship between a probe guard installation presence/absence detection sensor and a sensor detection surface 31 in a state before a probe guard in an example of the invention is moved in a vertical direction.
Figure 6:
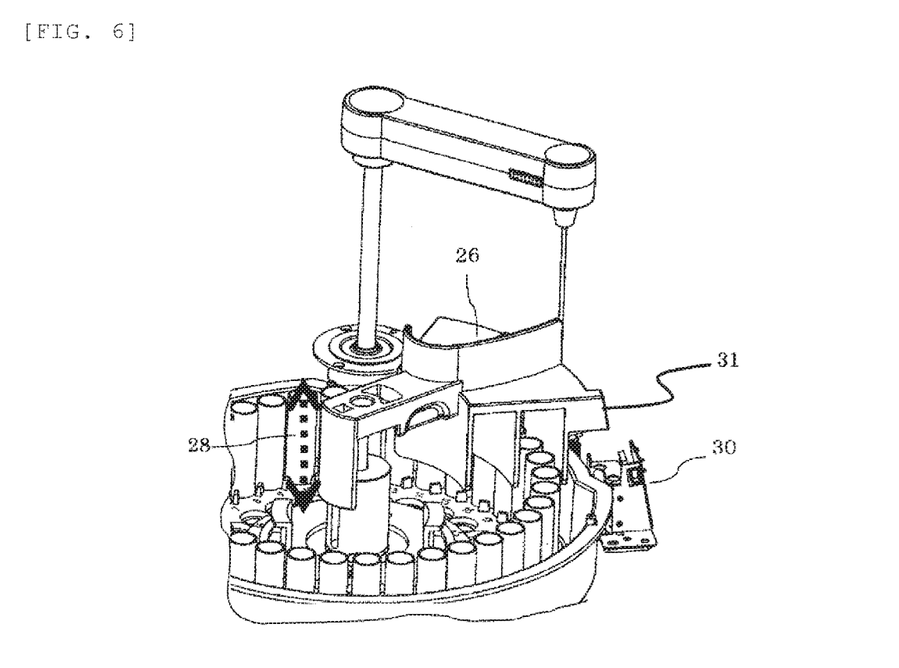
FIG. 6 shows a state after a probe guard in an example of the invention is moved in a vertical direction.

FIG. 5 shows a positional relationship between the probe guard installation presence/absence detection sensor 30 and the sensor detection surface 31 in a state before the probe guard 26 is moved in the vertical direction. FIG. 6 shows a state after the probe guard 26 is moved in the vertical direction.

In FIG. 5, the sensor detection surface 31 is an outer surface portion of a part in which the probe guard 26 is installed in the outer circumferential portion of the specimen container erection mechanism 1, and the probe guard installation presence/absence detection sensor 30 faces the sensor detection surface 31 to detect the sensor detection surface 31 and monitors installation of the probe guard 26 in the specimen container erection mechanism 1.

In FIG. 6, the probe guard 26 can be moved in the vertical direction 28, and, when the probe guard 26 is moved from an installation position, the probe guard installation presence/absence detection sensor 30 detects that the probe guard 26 has been removed from the installation position of the specimen container erection mechanism 1.

Figure 7:
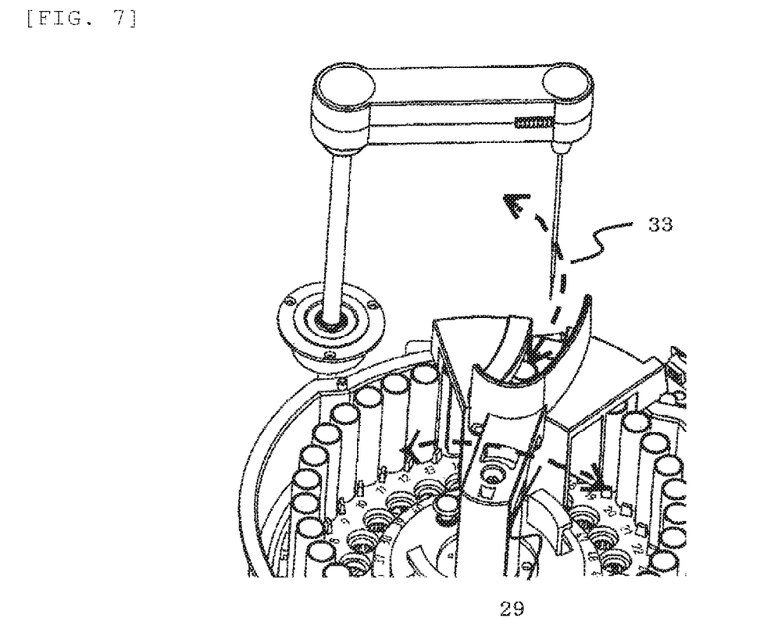
FIG. 7 shows a state in which a probe guard in an example of the invention is installed and a state in which the probe guard is moved in a horizontal direction.
Figure 8:
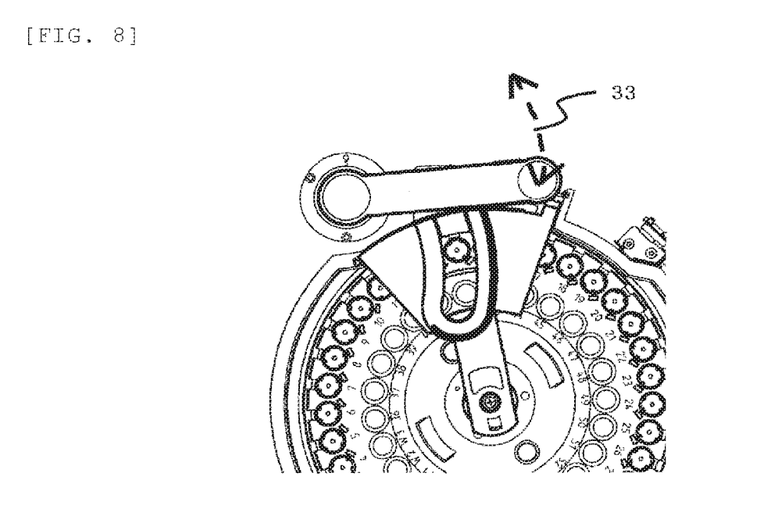
FIG. 8 shows a state in which a probe guard in an example of the invention is installed and a state in which the probe guard is moved in a horizontal direction.
Figure 9:
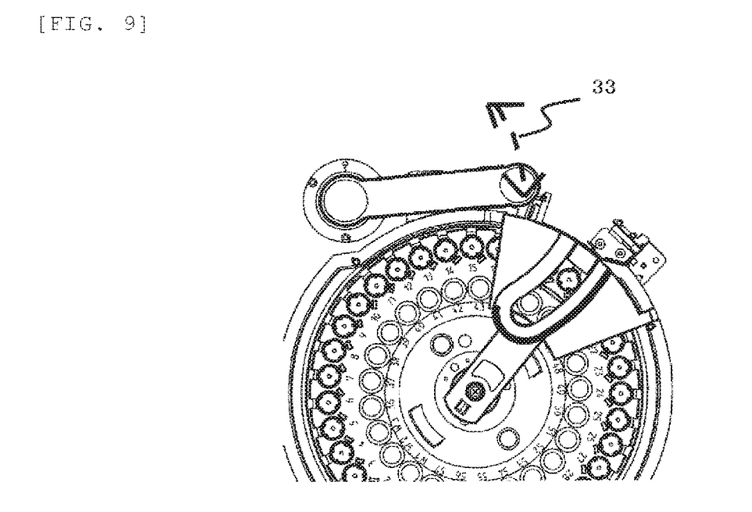
FIG. 9 shows a state in which a probe guard in an example of the invention is installed and a state in which the probe guard is moved in a horizontal direction.

FIG. 7, FIG. 8, and FIG. 9 show an installation state of the probe guard 26 and a state in which the probe guard 26 is moved in the horizontal direction. The probe guard 26 can be moved in the horizontal direction in a state in which the probe guard 26 is lifted up in the vertical direction as shown in FIG. 6. In the case where the probe guard 26 is moved in the horizontal direction, an outer circumferential wall 35 (shown in FIG. 11) is positioned on a probe moving track 33, and therefore contact between a user and a probe (sampling nozzle 23) is prevented and safety of the user is maintained.

Figure 10:
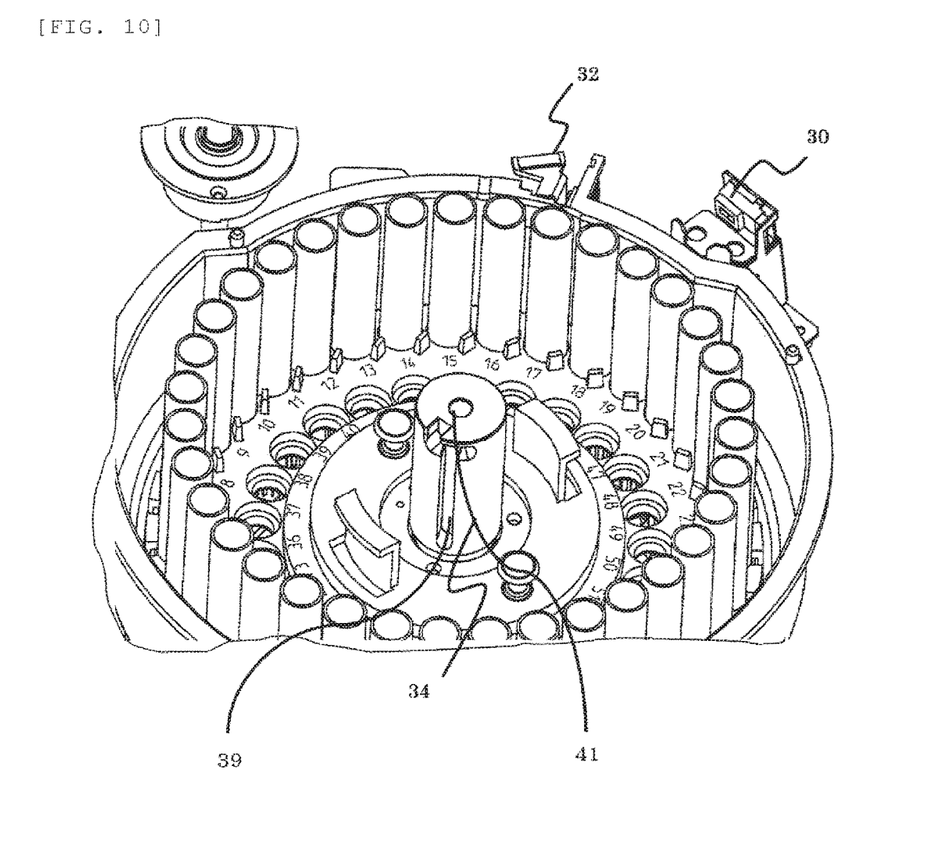
FIG. 10 shows a structure of a shutter, a probe guard installation presence/absence detection sensor, and a probe guard bearing in an example of the invention and a positional relationship thereamong.

FIG. 10 shows a structure of a shutter 32, the probe guard installation presence/absence detection sensor 30, and a probe guard bearing 34 and a positional relationship thereamong. In FIG. 10, the shutter 32 is arranged on an outer circumference of the specimen container erection mechanism 1, and, normally, in the case where the probe guard 26 is installed in the specimen container erection mechanism 1, the shutter 32 is positioned while being stored below the probe guard 26. In the case where the probe guard 26 is removed from the specimen container erection mechanism 1, the shutter 32 is moved upward from a storage position to be positioned on the probe moving track 33, and therefore safety of the user is maintained. Details thereof will be described with reference to FIG. 14 and FIG. 15.

The probe guard bearing 34 is positioned at the center of the specimen container erection mechanism 1 to limit installation, a moving direction, and a moving range of the probe guard 26. In the probe guard bearing 34, a shaft insertion hole 41 into which a shaft 40 of the probe guard 26 described below is inserted and a probe guard guide 39 into which a guide pin 36 described below is inserted are provided.

Figure 11:
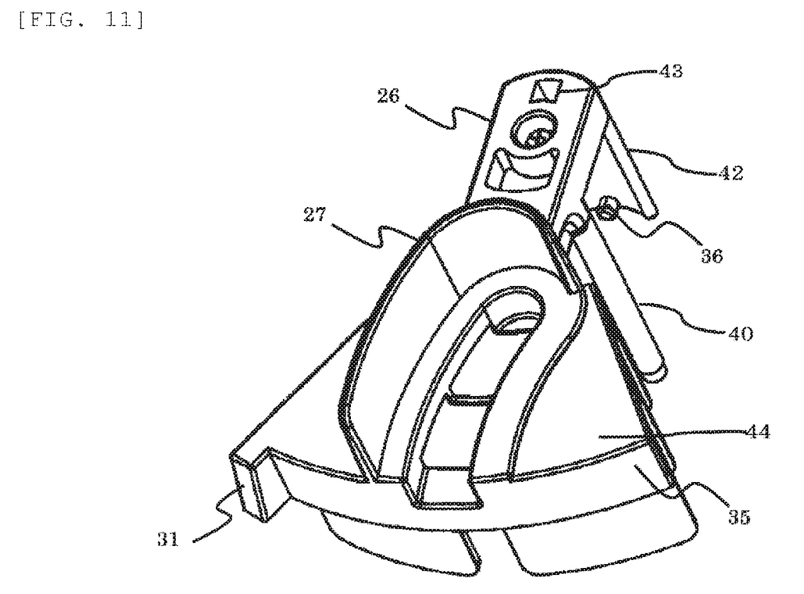
FIG. 11 shows a detailed part of a probe guard in an example of the invention.
Figure 12:
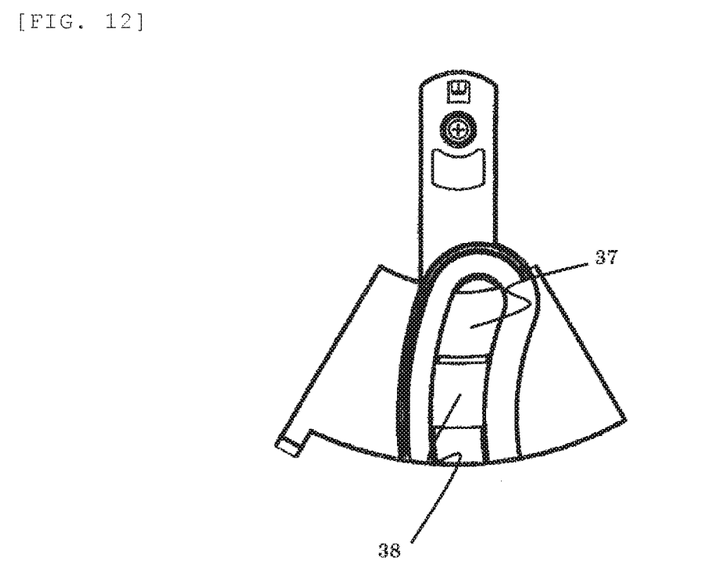
FIG. 12 shows a detailed part of a probe guard in an example of the invention.

FIG. 11 and FIG. 12 show a detailed part of the probe guard 26. In FIG. 11 and FIG. 12, the shaft 40 is inserted into the shaft insertion hole 41 of the bearing 34. This shaft 40 is provided on a support portion 43, and a guide plate 42 is a circular arc plate provided in an end portion of the support portion 43 and extending in parallel with the shaft 40. The guide pin 36 is provided on this guide plate 42. As described above, this guide pin 36 is inserted into the probe guard guide 39 of the bearing 34.

The guide pin 36 has a function for limiting the moving direction and the moving range of the probe guard 26 in combination with the probe guard guide 39 in the case where the probe guard 26 is installed in the probe guard bearing 34.

An inner circumferential dispensing port 37 and an outer circumferential dispensing port 38 are provided in a guard plate 44. Further, the guard wall 27 is provided on the guard plate 44. The guard wall 27 is a wall-shaped member parallel with the probe moving track of the specimen sampling mechanism 5 above the specimen container arrangement mechanism 1 and erected in an up-and-down direction.

The guard plate 44 has an access limiting part extending in the horizontal direction. The outer circumferential wall 35 extends in a direction parallel with the shaft 40 from an end portion of the guard plate 44. The outer circumferential wall 35 is held by the outer circumferential portion of the specimen container erection mechanism 1. Further, the sensor detection surface 31 is provided on an end surface of the outer circumferential wall 35.

The inner circumferential dispensing port 37 and outer circumferential dispensing port 38 described above are opening portions in the probe guard 26 for allowing the sampling nozzle 23 to access the specimen container 21 positioned below the probe guard 26.

Figure 13:
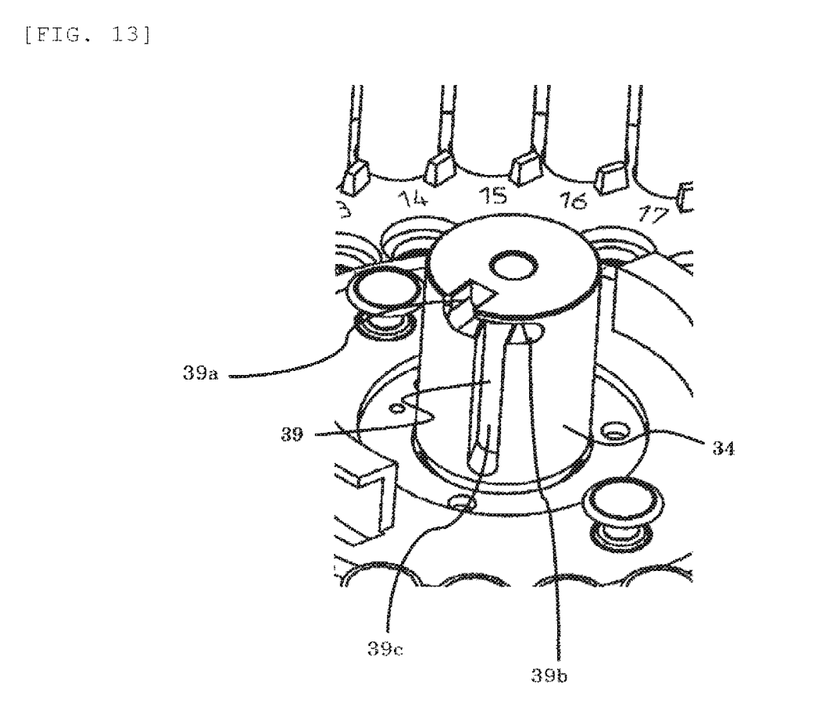
FIG. 13 shows a structure of a probe guard guide in a probe guard bearing in an example of the invention.

FIG. 13 shows a structure of the probe guard guide 39 in the probe guard bearing 34. The probe guard guide 39 has a groove shape for allowing the guide pin 36 shown in FIG. 11 to pass therethrough and limits the moving range of the probe guard 26 in the vertical and horizontal directions.

In other words, the probe guard guide 39 has an insertion and extraction groove 39a extending downward from a top surface of the probe guard bearing 34, a horizontal movement groove 39b communicating with this insertion and extraction groove 39a and extending in the horizontal direction, and a fixing groove 39c communicating with this horizontal movement groove 39b and extending in the vertical direction.

In the case where the probe guard 26 is attached to the specimen container erection mechanism 1, the shaft 40 of the probe guard 26 is inserted into the shaft insertion hole 41 of the bearing 34, and the guide pin 36 is inserted into the insertion and extraction groove 39a. Then, the guide pin 36 is moved in the horizontal direction along the horizontal movement groove 39b. Next, the guide pin 36 is moved in the vertical direction along the fixing groove 39c, and the shaft 40 is inserted into the shaft insertion hole 41.

In the case where the probe guard 26 is removed from the fixing groove 39c, the probe guard 26 is moved in an opposite direction of the above direction.

In the case where the probe guard 26 accesses the specimen container 21 without being removed from the specimen container erection mechanism 1, the guide pin 36 is moved upward along the fixing groove 39c and the guide pin 36 is moved in the horizontal direction along the horizontal movement groove 39b, and thus it is possible to access the specimen container 21. After access to the specimen container 21 is terminated, the guide pin 36 is moved downward along the fixing groove 39c, and thus it is possible to fix the probe guard 26 to the specimen container erection mechanism 1.

Figure 14:
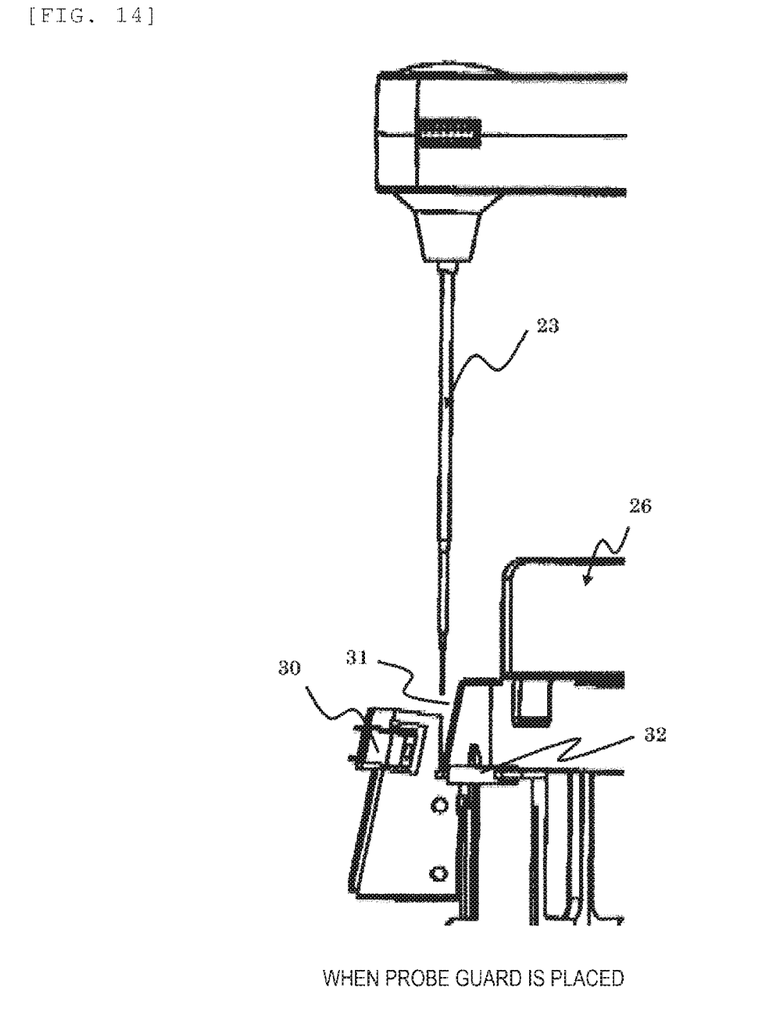
FIG. 14 shows a positional relationship among a sampling nozzle, a probe guard in an example of the invention, a probe guard installation presence/absence detection sensor, a sensor detection surface, and a shutter in a state in which the probe guard is attached to a specimen container erection mechanism.
Figure 15:
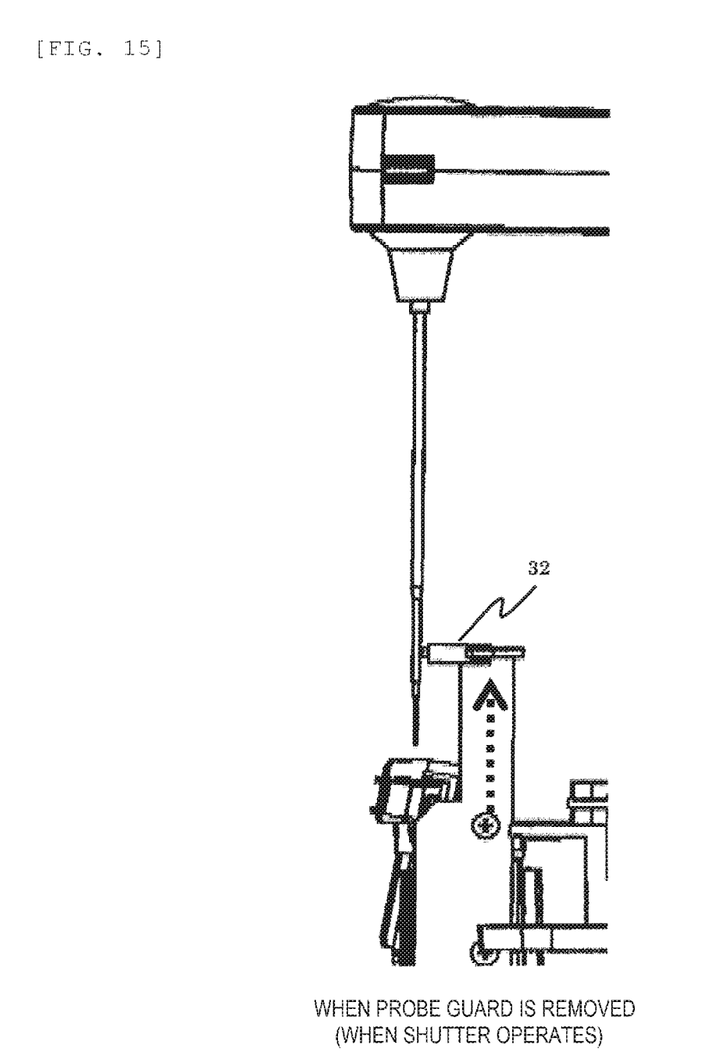
FIG. 15 shows a positional relationship among a sampling nozzle, a probe guard installation presence/absence detection sensor, a sensor detection surface, and a shutter in a state in which a probe guard in an example of the invention is removed from a specimen container erection mechanism.

FIG. 14 shows a positional relationship among the sampling nozzle 23, the probe guard 26, the probe guard installation presence/absence detection sensor 30, the sensor detection surface 31, and the shutter 32 in a state in which the probe guard 26 is attached to the specimen container erection mechanism 1. FIG. 15 shows a positional relationship among the sampling nozzle 23, the probe guard installation presence/absence detection sensor 30, the sensor detection surface 31, and the shutter 32 in a state in which the probe guard 26 is removed from the specimen container erection mechanism 1.

As shown in FIG. 14, in a state in which the probe guard 26 is attached to the specimen container erection mechanism 1, the shutter 32 is positioned below the probe guard 26 and the probe guard installation presence/absence detection sensor 30 and the sensor detection surface 31 are positioned to face each other. In the case where the probe guard installation presence/absence detection sensor 30 and the sensor detection surface 31 face each other, the probe guard installation presence/absence detection sensor 30 transmits a detection signal to the microcomputer 14 via the interface 13. Thus, the microcomputer 14 recognizes that the probe guard 26 is attached to the specimen container erection mechanism 1.

As shown in FIG. 15, in a state in which the probe guard 26 is removed from the specimen container erection mechanism 1, the shutter 32 is moved upward to be positioned on the probe moving track 33 (shown in FIG. 7 to FIG. 9). This prevents the sampling nozzle 23 from moving toward a user, and therefore safety of the user is maintained. Further, a signal for detecting the sensor detection surface 31 from the probe guard installation presence/absence detection sensor 30 is not transmitted to the microcomputer 14. With this, the microcomputer 14 recognizes that the probe guard 26 has been removed from the specimen container erection mechanism 1.

Figure 16:
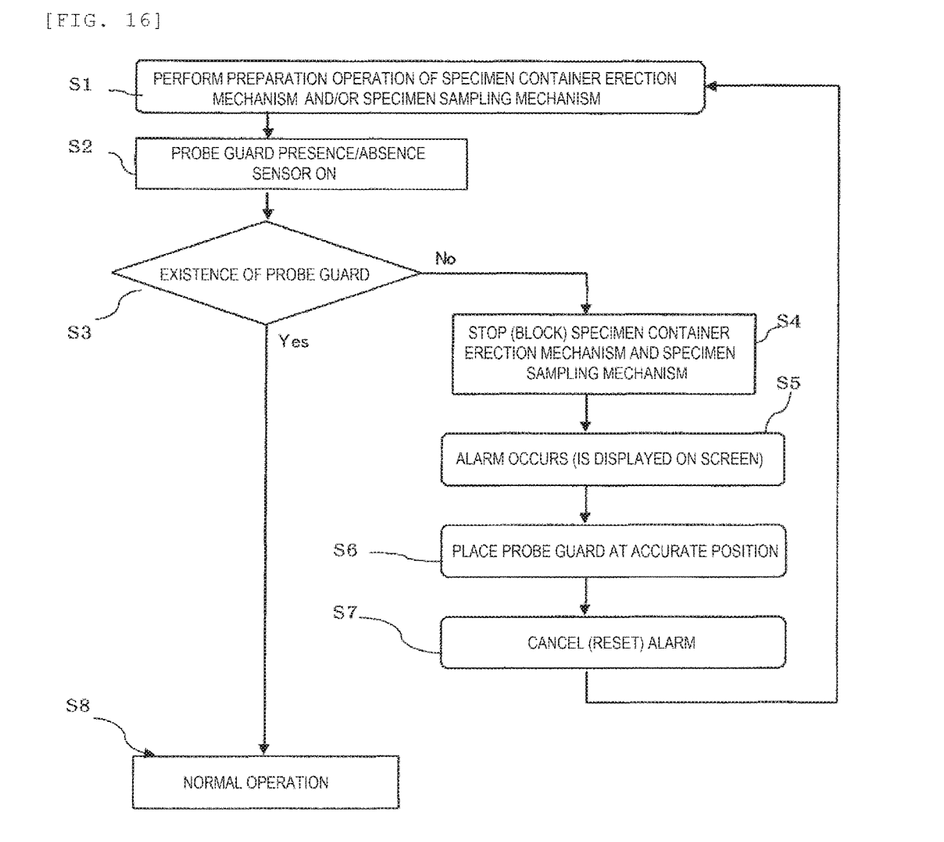
FIG. 16 is a flowchart showing an alarm generation logic using a probe guard installation presence/absence detection sensor in an example of the invention.

FIG. 16 is a flowchart showing an alarm generation logic using the probe guard installation presence/absence detection sensor 30.

In Step S1 of FIG. 16, operation preparation of the specimen container erection mechanism 1 and the specimen sampling mechanism 5 is performed by the automatic analysis device. Then, in Step S2, the probe guard installation presence/absence detection sensor 30 enters an operation state. Subsequently, in Step S3, the microcomputer 14 determines whether or not the probe guard installation presence/absence detection sensor 30 detects the probe guard 26. In the case where the probe guard installation presence/absence detection sensor 30 detects the probe guard 26 in Step S3, the processing proceeds to Step S8 and normal analysis operation is executed.

In the case where the probe guard installation presence/absence detection sensor 30 does not detect the probe guard 26 in Step S3, the processing proceeds to Step S4. Then, in Step S4, the microcomputer 14 stops operation of the specimen container erection mechanism 1 and the specimen sampling mechanism 5 (blocking the sampling nozzle 23 (probe) by using the shutter 32).

Then, in Step S5, the microcomputer 14 displays an alarm (warning about removal of probe guard) on the LCD 16 with a touchscreen.

When the microcomputer 14 detects that the probe guard 26 has been installed in a right position in Step S6, the processing proceeds to Step S7 and the microcomputer 14 cancels the alarm, and the processing returns to Step S1.

Also in the case where the probe guard 26 is removed from the specimen container erection mechanism 1 during analysis, and then the probe guard 26 is installed in the specimen container erection mechanism 1 again, and analysis operation is started again, an alarm can be added to analysis result data.

As in the above-mentioned operation, an alarm is displayed in the case where whether or not the probe guard 26 is installed is detected and the probe guard 26 is not installed. This makes it possible to maintain safety of a user.

As described above, according to an example of the invention, the probe guard 26 can be moved to a position above the specimen container erection mechanism 1 from a state in which the probe guard 26 is installed in the specimen container erection mechanism 1, and upward movement of the probe guard 26 is restricted by the horizontal movement groove 39b of the probe guard bearing 34 and movement thereof in the horizontal direction can be performed within a fixed range.

Thus, it is possible to access a specimen container guarded by the probe guard 26 in a state in which the probe guard 26 is attached to the specimen container erection mechanism 1. The moving direction of the probe guard 26 is an up-and-down direction (vertical direction) of the specimen container erection mechanism 1 and a horizontal direction within a region above the specimen container erection mechanism 1, and therefore it is possible to access the specimen container without moving the probe guard 26 to the outside of the region above the specimen container erection mechanism 1.

Therefore, it is possible to realize an automatic analysis device having a small moving range for accessing a specimen installation section and including a probe guard capable of moving without being removed from the specimen installation section. According to the invention, even in the case of a small automatic analysis device, it is possible to move a probe guard without removing the probe guard from a specimen container installation section (specimen container erection mechanism).

Further, according to an example of the invention, in the case where the probe guard 26 is removed from the specimen container erection mechanism 1, the shutter 32 can restrict movement of the sampling nozzle 23 (probe) and protect an operator from the sampling nozzle 23. This makes it possible to improve safety.

Note that, in the above-mentioned example, the probe guard 26 can be removed from the specimen container erection mechanism 1 by extracting the guide pin 36 from the insertion and extraction groove 39a and extracting the shaft 40 from the shaft insertion hole 41. However, a vertical and horizontal movement restriction section having another structure for restricting movement of the probe guard 26 in the vertical and horizontal directions may be provided in the bearing 34 and the support portion 43 of the probe guard 26.

For example, it is also possible to have a structure in which a flange-shaped member having a longitudinal groove is provided on an upper portion of an outer surface of the probe guard bearing 34 and the guide pin 36 is inserted into the longitudinal groove of the flange-shaped member. In this case, a stopper member for restricting rotation of the probe guard 26 can also be provided on the probe guard bearing 34.

Further, in the case where the probe guard bearing 34 has a columnar shape and the support portion 43 of the probe guard 26 has a cylindrical shape, it is possible to have a structure in which the probe guard 26 is supported by covering the columnar probe guard bearing 34 with the cylindrical support portion 43. In this case, a protruded portion is provided on the outer surface of the bearing 34 and a cross-shaped groove is provided in the cylindrical support portion 43, and the protruded portion provided on the outer surface of the bearing 34 is inserted into this groove. Thus, it is possible to restrict movement of the probe guard 26 in the vertical and horizontal directions.

Further, in the above-mentioned example, the probe guard 26 is supported by the specimen container erection mechanism (specimen container arrangement mechanism) 1. However, the probe guard can also be supported by the outer circumferential portion of the specimen container erection mechanism instead of the specimen container erection mechanism 1.

REFERENCE SIGNS LIST

1 . . . specimen container erection mechanism, 2 . . . reaction vessel mechanism, 3 . . . reagent cooling mechanism, 4 . . . thermostatic vessel, 5 . . . specimen sampling mechanism, 6 . . . reaction cell washing mechanism, 7 . . . photometer, 8 . . . stirring mechanism, 9 . . . reagent pipetting mechanism, 10 . . . sample dispensing control unit, 11 . . . washing water pump, 12 . . . reagent dispensing control unit, 13 . . . interface, 14 . . . microcomputer, 15 . . . Log converter/A/D converter, 16 . . . LCD with touchscreen, 17 . . . printer, 18 . . . storage medium, 19 . . . reaction cell, 20 . . . constant temperature maintaining device, 21 . . . specimen container, 22 . . . movable arm, 23 . . . sampling nozzle, 24 . . . reagent bottle, 25 . . . light source, 26 . . . probe guard, 27 . . . guard wall, 28 . . . specimen sampling mechanism track (vertical direction), 29 . . . specimen sampling mechanism track (horizontal direction), 30 . . . probe guard installation presence/absence detection sensor, 31 . . . sensor detection surface, 32 . . . shutter, 33 . . . probe track, 34 . . . probe guard bearing, 35 . . . outer circumferential wall, 36 . . . guide pin, 37 . . . dispensing port 1, 38 . . . dispensing port 2, 39 . . . probe guard guide, 39a . . . insertion and extraction groove, 39b . . . horizontal movement groove, 39c . . . fixing groove, 40 . . . shaft, 41 . . . shaft insertion hole, 42 . . . guide plate, 43 . . . support portion, 44 . . . guard plate

The invention claimed is:

1. An automatic analysis device, comprising:
a specimen container arrangement mechanism in which a specimen container is arranged, the specimen container arrangement mechanism being configured to move the arranged specimen container;
a reagent container arrangement mechanism in which a reagent container is arranged;
a reaction container arrangement mechanism in which a reaction container for reacting a specimen with a reagent is arranged;
a specimen sampling mechanism including a probe for sucking the specimen from the specimen container arranged in the specimen container arrangement mechanism and discharging the specimen to the reaction container arranged in the reaction container arrangement mechanism;
a reagent sampling mechanism configured to suck the reagent from the reagent container arranged in the reagent container arrangement mechanism and discharge the reagent to the reaction container arranged in the reaction container arrangement mechanism;

a photometer configured to analyze the specimen in the reaction container arranged in the reaction container arrangement mechanism;

a control unit configured to control operation of the specimen container arrangement mechanism, the reagent container arrangement mechanism, the reaction container arrangement mechanism, the specimen sampling mechanism, and the reagent sampling mechanism;

a probe guard having a guard wall for surrounding the probe when the probe of the specimen sampling mechanism positions above the specimen container arrangement mechanism; and a vertical and horizontal movement restriction section configured to restrict movement of the probe guard in vertical and horizontal directions in a state in which the probe guard positions above the specimen container arrangement mechanism, wherein the vertical and horizontal movement restriction section includes a bearing provided at a center portion of the specimen container arrangement mechanism and a support portion integrally provided with the guard wall of the probe guard and supported by the bearing of the specimen container arrangement mechanism, and the bearing and the support portion of the probe guard restrict movement of the probe guard in the vertical and horizontal directions in a state in which the support portion of the probe guard is supported by the bearing.

2. The automatic analysis device according to claim 1, wherein:

the support portion of the probe guard has a shaft, a guide plate extending in parallel with the shaft, and a guide pin provided on the guide plate;

the bearing has a shaft insertion hole, an insertion and extraction groove extending from a top surface of the bearing in an up-and-down direction, a horizontal movement groove communicating with the insertion and extraction groove and extending in the horizontal direction, and a fixing groove communicating with a center portion of the insertion and extraction groove and extending in the up-and-down direction; and the probe guard is supported by the bearing in such a way that the shaft of the probe guard is inserted into the shaft insertion hole and the guide pin provided on the guide plate is inserted into the horizontal movement groove, passes through the horizontal movement groove, and is inserted into the fixing groove.

3. The automatic analysis device according to claim 1, wherein the guard wall of the probe guard is a wall-shaped member parallel with a moving track of the probe of the specimen sampling mechanism above the specimen container arrangement mechanism and erected in an up-and-down direction.

4. The automatic analysis device according to claim 1, wherein the probe guard is held by a center portion of the specimen container arrangement mechanism and an outer circumferential portion of the specimen container arrangement mechanism.

5. The automatic analysis device according to claim 4, further comprising a sensor configured to detect whether or not the probe guard is held by the specimen container arrangement mechanism.

6. The automatic analysis device according to claim 1, wherein in the case where the control unit detects that the probe guard is not held by the specimen container arrangement mechanism on the basis of a signal from a sensor, the control unit stops operation of the specimen sampling mechanism and the specimen container arrangement mechanism.

7. An automatic analysis device, comprising:

a specimen container arrangement mechanism in which a specimen container is arranged, the specimen container arrangement mechanism being configured to move the arranged specimen container;

a reagent container arrangement mechanism in which a reagent container is arranged;

a reaction container arrangement mechanism in which a reaction container for reacting a specimen with a reagent is arranged;

a specimen sampling mechanism including a probe for sucking the specimen from the specimen container arranged in the specimen container arrangement mechanism and discharging the specimen to the reaction container arranged in the reaction container arrangement mechanism;

a reagent sampling mechanism configured to suck the reagent from the reagent container arranged in the reagent container arrangement mechanism and discharge the reagent to the reaction container arranged in the reaction container arrangement mechanism;

a photometer configured to analyze the specimen in the reaction container arranged in the reaction container arrangement mechanism;

a control unit configured to control operation of the specimen container arrangement mechanism, the reagent container arrangement mechanism, the reaction container arrangement mechanism, the specimen sampling mechanism, and the reagent sampling mechanism;

a probe guard having a guard wall for surrounding the probe when the probe of the specimen sampling mechanism positions above the specimen container arrangement mechanism; and a vertical and horizontal movement restriction section configured to restrict movement of the probe guard in vertical and horizontal directions in a state in which the probe guard positions above the specimen container arrangement mechanism, wherein the probe guard has a support portion supported by a center portion of the specimen container arrangement mechanism and an outer wall portion supported by an outer circumferential portion of the specimen container arrangement mechanism, and the outer wall portion of the probe guard positions on a track of the probe of the specimen sampling mechanism within a range in which the probe guard is moved around the support portion in the vertical direction and the horizontal direction so that the outer wall portion prevents the probe from entering a position above the specimen container arrangement mechanism.

8. The automatic analysis device according to claim 2, further comprising a shutter arranged on the side of an outer circumferential portion of the specimen container arrangement mechanism, the shutter being moved to a track of the probe when the probe guard is removed from the specimen container arrangement mechanism so as to prevent the probe from entering a position above the specimen container arrangement mechanism.

9. The automatic analysis device according to claim 2, wherein the automatic analysis device further includes a probe guard installation presence/absence detection sensor configured to detect whether or not the probe guard is attached to the specimen container arrangement mechanism and a display section, wherein the control unit displays an alarm on the display section in the case where the probe guard installation presence/absence detection sensor detects that the probe guard is not attached to the specimen container arrangement mechanism.

10. The automatic analysis device according to claim 9, wherein when, during specimen analysis operation, the probe guard installation presence/absence detection sensor detects that the probe guard has been removed from the specimen container arrangement mechanism and the probe guard has been attached to the specimen container arrangement mechanism again, the control unit adds an alarm to analysis result data of the specimen analysis operation and displays the alarm on the display section.

\* \* \* \* \*